United States Patent [19]

Lepage

[11] Patent Number: 5,605,535
[45] Date of Patent: Feb. 25, 1997

[54] ANKLE POSITIONING SPLINT

[76] Inventor: Jeffrey A. Lepage, 7067 S. 2155 East, Salt Lake City, Utah 84121

[21] Appl. No.: 432,085

[22] Filed: May 1, 1995

[51] Int. Cl.$^6$ ............................................. A61F 5/00
[52] U.S. Cl. ................................... 602/27; 602/23
[58] Field of Search ........................... 602/23, 27, 65, 602/5, 16; 128/882

[56] References Cited

U.S. PATENT DOCUMENTS

| | | | |
|---|---|---|---|
| 4,497,070 | 2/1985 | Cho | 602/27 |
| 4,587,962 | 5/1986 | Greene et al. | 602/27 |
| 4,646,726 | 3/1987 | Westin et al. | 602/27 |
| 4,693,239 | 9/1987 | Clover, Jr. | 602/27 |
| 4,919,118 | 4/1990 | Morris | 602/27 |
| 5,069,202 | 12/1991 | Prock | 602/27 |
| 5,094,232 | 3/1992 | Harris et al. | 602/27 |
| 5,125,400 | 6/1992 | Johnson, Jr. | 602/27 X |
| 5,209,722 | 5/1993 | Miklaus et al. | 602/27 |
| 5,219,324 | 6/1993 | Hall | 602/27 |
| 5,242,378 | 9/1993 | Baker | 602/27 X |

OTHER PUBLICATIONS

Sammons, Your Complete Source For Orthopedic and ADL Products, Western Springs, IL, 1995, p. 236.
Alimed, Orthopedic–Rehabilitation 1994–1995, Dedham, MA, 1994, p. Q55.
Alimed, Orthopedic–Rehabilitation 1994–1995, Dedham, MA, 1994, p. Q83.
Alimed, Orthopedic–Rehabilitation 1994–1995, Dedham, MA, 1994, p. R34.
Alimed, Orthopedic–Rehabilitation 1994–1995, Dedham, MA, 1994, p. R36.
Alimed, Orthopedic–Rehabilitation 1994–1995, Dedham, MA, 1994, p. R35.

Smith & Nephew Roylan Rehabilitation Products Catalog 1995, Germantown, WI, 1995, p. 130.
Smith & Nephew Roylan Rehabilitation Products Catalog 1995, Germantown, WI, 1995, p. 131.
Orthomerica Products, Inc. 1995 Product Catalog, Orlando, FL, 1995, P. 29.
This Splint Will Go To Any Length To Prevent Foot Drop, Maitland, FL, 1995, Flyer.

*Primary Examiner*—Richard J. Apley
*Assistant Examiner*—Kim M. Lee
*Attorney, Agent, or Firm*—Thorpe, North & Western, L.L.P.

[57] ABSTRACT

An ankle positioning splint. The splint includes a load-bearing foot brace having a bottom plate for supporting a foot in a supported position against the plate. A pair of splint arms extend upwardly from the plate and along opposing sides of the lower leg, respectively. A heel strap and an anterior ankle strap are secured to the foot brace means at opposing positions. The anterior ankle strap presses against the anterior ankle, and the heel strap presses against a specific rear portion of the heel posterior to the ankle and adjacent the calcaneus. The heel strap conforms to the natural curvature of the angled rear portion of the heel so as to apply a specific downward force into the calcaneus, and preferably does not circumscribe the foot or the leg. A calf strap is secured to the splint arms for pressing against the angled upper section of the calf muscle. The calf strap preferably does not circumscribe the leg, and is counteracted by a front strap which presses against the front of the lower leg just below the knee. The straps and all surfaces of the brace that contact the foot and leg are heavily padded, and an optional middle strap can be disposed on the splint arms to circumscribe the leg at a location between the calf strap and the heel strap for additional support.

32 Claims, 2 Drawing Sheets

ANKLE POSITIONING SPLINT

BACKGROUND OF THE INVENTION

1. The Field of the Invention

The present invention relates generally to lower extremity orthoses. More particularly, it concerns an ankle positioning splint for patients confined to permanent bedrest, or individuals at risk for ankle plantar flexion contractures (heal cord tendon shortening), or individuals with neurologic conditions that have resulted in pathological increases in muscle tone in the lower extremities.

2. The Background Art

Individuals confined to bedrest, even for brief periods of time, are at substantial risk of developing muscle shortening or contractures. It will be appreciated that the human foot tends to plantar flex to a pointed position during periods of rest whereby the foot moves in the plantar-flexion range of motion (see FIG. 5). Plantar-flexion range of motion refers to movement of the foot downward from a neutral position to some position within approximately 60 degrees of the neutral position. The neutral position refers to the foot being positioned at approximately 90 degrees relative to the lower leg.

If plantar-flexion is allowed to occur for longer than 4 to 5 days, the tendons and ligaments shorten, resulting in a contracture of the ankle joint. One resulting problem is that patients who are comatose or otherwise bedridden for long periods of time experience what is known as "ankle plantar flexion contracture", whereby the tendons and ligaments in the leg effectively shorten into their naturally biased contracted position so that the foot cannot dorsiflex appropriately for ambulation, or allow the individual to walk without a great amount of pain.

Athletes or any other active persons, that is individuals who are involved in weekend sports such as tennis or who exercise on a regular basis (especially on an intermittent basis) may experience heal cord tightness and/or plantar fascitis of the feet. Both conditions are usually very painful. Holding the ankle in the neutral or 90 degree position during sleep helps prevent these painful conditions.

The neurologic patient (an individual with a head injury, either traumatic or vascular in nature), or an individual who has suffered a spinal cord injury, often develops what is termed "hyper-tonicity" of certain muscle groups. Such individuals frequently develop hyper plantar flexion of the ankle joint in both legs. Maintaining the ankle in the neutral position can prevent plantar flexion contractures at the ankle in such individuals.

When contracture occurs at the ankle it is difficult if not impossible for the individual to walk. Attempting to walk with ankle plantar flexion contractures is very painful. Walking with ankle plantar flexion contracture also poses a significant risk of tearing the muscle tendons of the calf muscles (medically termed gastroc-soleus complex, or more commonly the Achilles tendon or heel cord).

Conventional treatment of ankle plantar flexion contractures is performed by physical therapists and other caregivers, and is referred to as "passive range of motion". This treatment involves moving the foot or ankle joint periodically and requires a great deal of force. The purpose of the treatment is to stretch the ligaments and tendons to cause the ankle and foot to assume at least the neutral position. The ultimate goal of this therapy is to allow the ankle joint to move into what is known as "dorsi-flexion" range of motion which will allow normal ambulation (i.e. walking). Dorsi-flexion range of motion is the movement of the foot from the neutral position to a position closer to the leg or up toward the leg (see FIG. 5). Dorsi-flexion range of motion normally involves approximately 20 degrees of movement. Unfortunately, performing passive range of motion on a contractured joint poses a risk of tearing or otherwise damaging the tendons and ligaments in the leg. This treatment approach is very laborious and time consuming and does not always restore the ankle and foot to the neutral position.

It has been discovered that maintaining the foot of a bedridden or neurologic patient in the neutral position inhibits development of contracture. Ankle splint devices have been developed in attempts to hold the foot in the neutral position during periods of bedrest. However, the prior art splint devices are characterized by a number of disadvantages. The natural biasing forces of the foot and leg (and especially the forces caused by hyper tonicity in the neurologic patient) are so great that the foot and leg tend to migrate out of the splint so that the foot returns to its natural biased position anyway. The prior art splint devices have been either ineffective to counteract the muscular forces of the leg, or the straps must be so tight that the patient does not tolerate it or circulation is cut off in the foot and severe pressure sores develop. These problems also hold true for prior art night splints for the athletic conditions of heel cord tightness and plantar fascitis.

OBJECTS AND SUMMARY OF THE INVENTION

It is therefore an object of the present invention to provide an ankle positioning splint which is effective in counteracting the natural biasing forces of the foot in the bedridden individual, as well as the hyper tonicity of the neurologic patient and the tightness and/or plantar fascitis of the more active population.

It is an additional object of the invention to provide such an ankle positioning splint that is comfortable while maintaining the foot/ankle in a neutral position and which is less likely to produce pressure sores on a patient.

It is another object of the invention to provide such an ankle positioning splint which is simple in design and manufacture.

It is a further object of the invention to provide such an ankle positioning splint which utilizes the inherent surface geometry of the foot and leg in preventing migration of the foot/leg out of the splint.

The above objects and others not specifically recited are realized in a specific illustrative embodiment of an ankle positioning splint. The splint includes a load-bearing foot brace having a bottom plate for maintaining a patient's foot in a supported position against the plate. The foot brace includes a pair of splint arms extending upwardly from the plate and along opposing sides of the lower leg, respectively, when the foot is in the foot brace/splint. A foot strap and a heel strap are secured to the foot brace at opposing positions. The foot strap presses against the foot anterior to the ankle, and the heel strap presses against the angled rear portion of the heel adjacent the calcaneus. The heel strap is configured and arranged to apply a specific counteracting force against the upper curve of the heel so that at least one non-frictional component of the force is directed toward the bottom plate of the foot brace and into the calcaneus. The heel strap preferably does not circumscribe the foot or the leg. A calf strap is secured to the splint arms for pressing against a posterior portion of the lower leg residing between the knee joint and the larger portion of the calf section. The calf strap preferably does not circumscribe the leg, and is counteracted by a front strap secured to the front of the splint arms for pressing against the front of the lower leg just below the knee. All straps and components of the brace that contact the foot, ankle or leg are heavily padded, and an optional middle strap can be disposed on the splint arms to circumscribe the leg at a location between the calf strap and the heel strap.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

Figure 1:
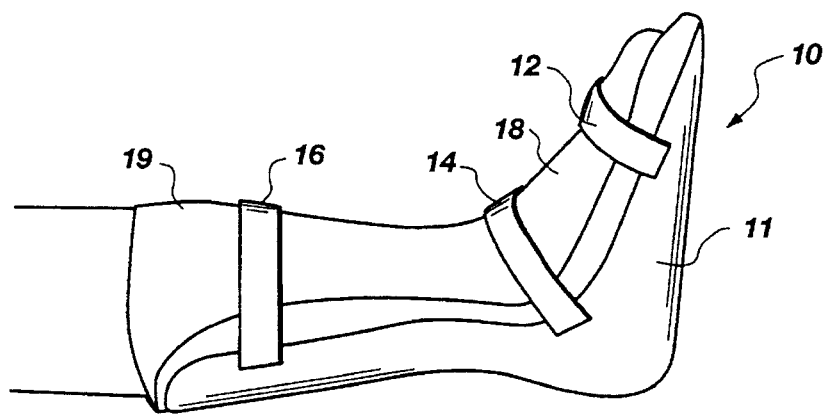
FIG. 1 is a side view of a prior art splint device secured to a patient's foot and lower leg.

For the purposes of promoting an understanding of the principles in accordance with the invention, reference will now be made to the embodiment illustrated in the drawings and specific language will be used to describe the same. It will nevertheless be understood that no limitation of the scope of the invention is thereby intended. Any alterations and further modifications of the illustrated device, and any additional applications of the principles of the invention as illustrated herein, which would normally occur to one skilled in the relevant art and possessed of this disclosure, are to be considered within the scope of the invention claimed.

Figure 4:
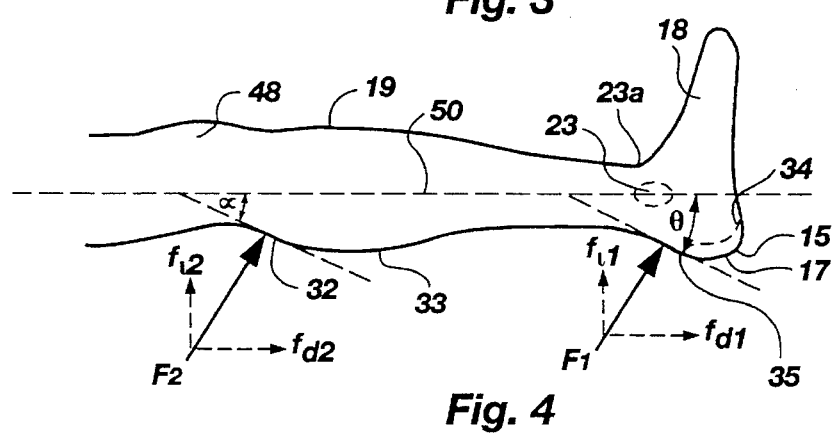
FIG. 4 is a schematic illustration of a force diagram of forces applied to a patient's leg by the ankle positioning splint of FIGS. 2 and 3.
Figure 5:
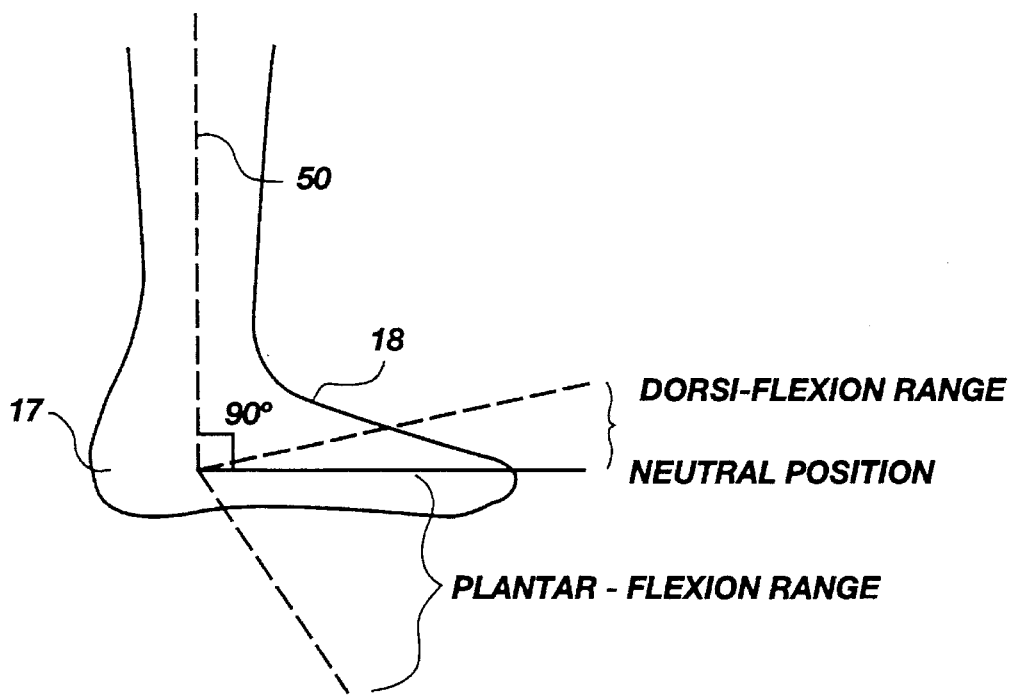
FIG. 5 is a side view of a foot showing different ranges of motion thereof.

Referring now to FIGS. 1 and 4, there is shown a prior art splint device, designated generally at 10. The splint device 10 includes a foot base 11 and straps 12, 14 and 16, and is intended to hold the foot 18 in a stretched position as shown so as to prevent the foot from returning to its natural biased position. The splint device 10 attempts to maintain the foot 18 in the neutral position (i.e. approximately 90 degrees relative to the leg) so that the tendons and ligaments within the lower leg 19 and ankle 23 remain lengthened to prevent contracture from developing.

Applicant has found the prior art splint devices such as the splint device 10 to be inadequate for their intended purpose. The splint device 10 simply fails to prevent the patient's heel from migrating out of the foot base 11. When the heel migrates out of the base 11, the foot 18 returns to its naturally biased pointed position with the undesired result of the tendons and ligaments becoming contracted. If the foot is not returned to a stretched position (such as the 90 degree neutral position shown), contracture will develop.

The natural biasing forces of the foot are so great that the straps 12, 14 and 16 are ineffective in keeping the heel of the foot supported against the foot base 11. It has been common practice for the upper strap 16 to be placed around the front of the leg 19 opposite the lower calf area, and for the ankle strap 14 to extend over the front curvature over the foot 18 as shown in FIG. 1. These prior art straps 12, 14 and 16 have been either ineffective to counteract the natural biasing forces of the foot, or the ankle strap 14 must be so tight that the individual does not tolerate it or circulation is cut off in the foot 18, causing the development of pressure sores such as decubitus ulcers.

Figure 2:
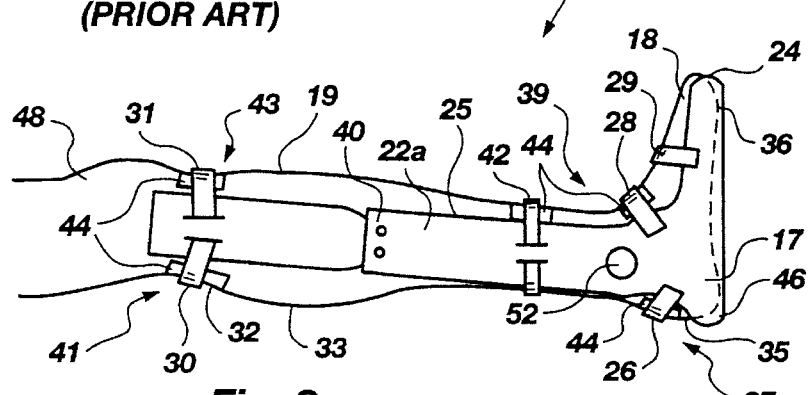
FIG. 2 is a side view of an ankle positioning splint, made in accordance with the principles of the present invention and being secured to a patient's foot and lower leg.
Figure 3:
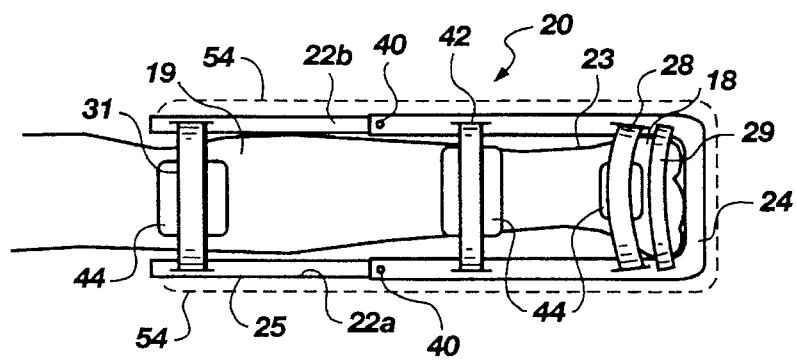
FIG. 3 is a front view of the ankle positioning splint of FIG. 2.

Until now, no other splint device known to applicant has been designed to take advantage of the inherent surface geometry of the foot and lower leg. Referring now to FIGS. 2–4, the invention subsists in an improved ankle positioning splint, designated generally at 20. The splint 20 includes one-piece unitary foot brace means 25 comprising first and second splint arms 22a and 22b positioned against opposing sides of the lower leg 19 and being intercoupled at their lower ends by a bottom plate 24. The foot brace means 25 is made from load-bearing material, such as rigid or semi-rigid resin-based thermoplastic. The improved splint 20 includes a heel strap 26, an ankle strap 28, a calf strap 30, an upper leg strap 31 and a middle strap 42. A foot strap 29 is included in the preferred embodiment. Any suitable support means may be used for any of these straps, including cloth straps, or rigid bands which are separately attached to the foot brace means 25 or integrally formed therewith in a unibody construction.

It will be appreciated that the foot brace means 25 is intended to comprise any suitable leg supporting means which extends upwardly from the plate 24 and along opposing sides of the lower leg 19, and which preferably include lower rear and front openings 37 and 39, respectively, and upper rear and front openings 41 and 43, respectively. Although the preferred embodiment comprises the dual splint arms 22a and 22b which are inherently open in the upper and lower rear and front portions as shown in the drawings, other embodiments such as a cylindrical brace having upper and lower front and rear openings formed specifically therein are also in accordance with the principles of the present invention.

The words "posterior" and "anterior" as used herein refer respectively to locations behind and in front of the ankle 23 or leg 19. Item 23a refers to the anterior ankle, or a portion of the body residing anterior to the ankle 23. The heel strap 26 is secured to opposing portions of the foot brace means 25 as shown, opposite the ankle strap 28 which is secured separately to other opposing portions of the foot brace means. The calf strap 30 is preferably secured to opposing portions of the splint arms 22a and 22b, opposite the upper leg strap 31 which is secured separately to other opposing portions of the splint arms. The middle strap 42 resides between the calf strap 30 and the heel strap 26, and is disposed on the splint arms 22a and 22b so as to circumscribe the lower leg 19.

Each strap 30 and 31 preferably intercouples the splint arms 22a–b without circumscribing the lower leg 19. Similarly, each strap 26 and 28 preferably intercouples opposing lower portions of the foot brace means 25 without circumscribing any portion of the foot 18 or leg 19. The heel strap 26 presses against a posterior portion of the foot 18 to aid in preventing substantial migration of the heel 17 away from the bottom plate 24. The ankle strap 28 presses against the foot 18 at a location anterior to the ankle 23. The calf strap 30 presses against a posterior extremity 32 of the lower leg 19 residing between the knee joint 48 and the larger portion 33 of the calf section to aid in preventing substantial migration of the heel 17 away from the bottom plate 24. The upper leg strap 31 presses against an anterior portion of the lower leg 19 at a location substantially opposite the calf strap 30.

It is to be understood that the ankle strap 28 and foot strap 29 function as foot holding means disposed on the foot brace means 25 for pressing against the anterior ankle 23 and the foot 18 respectively, and that any suitable foot holding means may be used in lieu of, or in addition to, these straps 28 and 29. For example, the foot brace means 25 may alternatively include integral bands (not shown) formed therein.

The splint 20 is preferably heavily padded, as illustrated schematically by pads 44. Preferably, all straps and any other portions of the splint 20 which contacts the foot or leg are heavily padded. The foot brace means 25 is configured for supporting the foot 18 in a supported position against the bottom plate 24. The patient's heel 17 is preferably suspended in any suitable manner, such as by provision of a padded heel cup 46, to prevent pressure on the lower posterior heel area 17.

One of the principal novelties of the invention includes the heel and calf straps 26 and 30, both alone and in combination. These straps 26 and 30 are specifically secured in angled positions to apply specifically directed forces at the heel and above the calf respectively. Referring now to FIGS. 1 and 4, when the natural bias of the foot 18 operates to exert pressure by the ball 36 of the foot against the bottom plate 24, the heel strap 26 applies a specific and opposing counteracting force $F_1$ at an angled posterior extremity 35 of the heel 17. At least part of this force $F_1$ passes into the calcaneus bone 34 (represented schematically in phantom line in FIG. 4). The calf strap 30 applies a specific counteracting force $F_2$ upon an angled posterior extremity 32 of the lower leg 19 residing between the knee joint 48 and the larger portion 33 of the calf section.

The advantageous effect is that the straps 26 and 30 are respectively configured and angled to conform to the curved surface geometry of the lower leg 19 at the posterior heel extremity 35 adjacent the calcaneus bone area 34 and at the posterior leg extremity 32 to hold the improved splint 20 in position such that the foot 18 remains firmly supported against the bottom plate 24. Because of their angled design, the straps 26 and 30 provide non-frictional components of force which applicant has found to be much more effective in preventing the foot 18 from migrating out of the splint 10. The ankle 23 is thereby maintained in a therapeutically stretched position, preferably at approximately 90 degrees relative to the lower leg 19. The improved splint 20 can be enhanced by adjustment structure 40 which allows the splint arms 22 to be selectively extended or retracted so as to fit a wide range of legs.

It will be appreciated that the improved splint 20 uses the inherent curvature of the calf area 32 and posterior heel area 35 to prevent migration of the heel 17 away from the bottom plate 24. The larger portion 33 of the calf and the lower knob 15 of the heel 17 act as seating areas which are respectively larger than the straps 30 and 26 so as to block the straps from slipping. The strap 30 simply cannot fit over the larger portion 33 of the calf, and the strap 26 cannot fit over the lower knob 15 of the heel 17. This prevents the foot and leg from migrating of the improved splint 20. By comparison, the prior art splint 10 in FIG. 1 must rely almost exclusively upon frictional engagement of the straps 12, 14 and 16 against the foot 18 and lower leg 19, which facilitates migration of the heel 17 away from the foot base 11 and causes shear forces on the anterior of the leg. Applicant's improved foot splint 20 provides the additional assistance of downwardly-directed forces $f_{d1}$ (from strap 26) and $f_{d2}$ (from strap 30), as explained below in more detail.

The posterior heel extremity 35 forms a first angle θ relative to the lower leg 19, with respect to a central axis 50 of the lower leg. The heel strap 26 is configured and arranged to seat firmly against the posterior heel extremity 35 such that at least a portion of the heel strap contacting the extremity 35 resides common to the first angle θ, and preferably such that substantially the entire heel-contacting portion of the heel strap resides common to the first angle. The heel strap 26 thereby exerts the counteracting force $F_1$ which passes through the heel 17 and into the calcaneus 34. Those of ordinary skill in the physics of vector analysis will appreciate that the counteracting force $F_1$ is divided into a downward component $f_{d1}$ and a lateral component $f_{l1}$. At least part of the downward component $f_{d1}$ is a non-frictional component of force which is conveyed toward the bottom plate 24 in a substantially parallel alignment with respect to the lower leg 19 (i.e. parallel with the lower leg axis 50).

In similar fashion, the posterior extremity 32 of the lower leg 19 residing between the knee joint 48 and the larger portion 33 of the calf section forms a second angle α relative to the lower leg 19, with respect to the central axis 50. The calf strap 30 is configured and arranged to seat firmly against the posterior extremity 32 such that a portion of the strap 30 contacting the posterior extremity 32 resides common to the second angle α. The calf strap 30 thereby exerts the counteracting force $F_2$ against the posterior extremity 32, which is divided into a downward component $f_{d2}$ and a lateral component $f_{l2}$. At least part of the downward component $f_{d2}$ is a non-frictional component of force which is conveyed toward the bottom plate 24 in a direction substantially parallel with the lower leg 19 (i.e. parallel with the lower leg axis 50).

The prior art splint devices 10 such as that shown in FIG. 1 fail to provide any structure which produces the downward components $f_{d1}$ or $f_{d2}$, because they lack applicant's specifically angled and configured rear straps 26 and 30. The prior art splint device 10 must rely upon the mere shear force or lateral friction provided by the strap 16 and the forces provided by the straps 12 and 14 which are not supported against migration-preventing geometry of the heel or calf. The result is that the natural biasing forces of the foot and leg overcome the inadequate forces provided by the prior art combination of straps 12, 14 and 16, the foot works its way partially out of the device 10, and contracture is not prevented.

Because applicant's preferred heel strap 26 and calf strap 30 are secured at their opposing ends to opposing portions of the foot brace means 25 without circumscribing the ankle 23 or leg 19, they can be configured to prevent substantial migration of the heel 17 away from the bottom plate 24 by being supported at their respective angles θ and α so as to conform to the inherent shape of the posterior heel extremity 35 and upper posterior calf extremity 32, respectively. The heel strap 26 may even be configured such that the portion contacting the posterior heel extremity 35 resides below the ankle joint 23. The calf strap 30 and upper leg strap 31 are preferred, but optional, as are the middle strap 42 and the upper leg strap 31.

As shown in FIGS. 2 and 4, the heel strap 26 presses against a posterior portion 35 of the patient's foot which resides forwardly of the lower posterior knob extremity 15 of the heel 17, such that the lower posterior knob extremity 15 extends rearwardly to a location beneath and rearward of the portion of the heel strap 26 which is pressing against the posterior portion 35 when the patient's foot 18 is supported against the bottom plate 24 in a supported position. This is illustrated most particularly by the position of arrow $F_1$ upon the posterior extremity 35 of the heel 17. The heel strap 26 is preferably disposed at an acute angle with respect to the bottom plate 24. Similarly, the calf strap 30 presses against a posterior portion 32 of the lower leg which resides forwardly of the larger portion 33 of the calf such that the larger portion 33 extends rearwardly to a location beneath and rearward of the portion of the calf strap 30 which is pressing against the posterior portion 32.

As also shown in FIGS. 2 and 4, the heel strap 26 preferably bisects and extend across the rear opening 37 at a location adjacent to the foot 18 such that the heel strap 26 divides the rear opening 37 into upper and lower openings. Further, the ankle strap 28, the foot brace means 25, and the portion of the heel strap 26 which presses against the posterior portion 35 cooperatively define an interior circumferential distance which is less than any circumferential distance of the foot that traverses both the rear-most portion of the lower posterior knob extremity 15 (as specifically indicated at the tip-end of the leadline of reference numeral 15) and the anterior ankle portion 23a of the foot 18, as indicated by inspection of FIGS. 2 and 4.

The improved splint 20 can be defined in many other ways which are supported by the drawings and the understanding brought thereby to those of ordinary skill in the relevant art. For example, at least a portion of the heel strap 26 resides above the heel 17 and closer to the lower leg axis 50 than the heel, to thereby block migration of the heel away from the bottom plate 24 of the foot brace means 25 when the foot 18 resides in the supported position. Further, at least a portion of the calf strap 30 resides above the larger portion 33 of the calf section and closer to the lower leg axis 50 than the larger calf portion to thereby block migration of the lower leg 19, and thus the heel 17, away from the bottom plate 24 of the foot brace means 25 when the foot 18 resides in the supported position.

It is to be understood that it is in accordance with the principles of the present invention for the improved splint 20 to include the heel strap 26 but not the calf strap 30, in which case the heel strap 26 acts alone to accomplish the purpose of the invention. Alternatively, the improved splint 20 may include just the calf strap 30 but not the heel strap 26, in which case the calf strap 30 acts alone to accomplish the purpose of the invention. Those having skill in the relevant art will understand from the present disclosure that the invention can be accomplished with any embodiment of the foot brace means 25 which includes any suitable foot holding means, such as the ankle strap 28 and foot strap 29, and either (i) the heel strap 26, or (ii) the calf strap 30. However, applicant has found that the preferred embodiment includes both the heel strap 26 and the calf strap 30.

Figure 6:
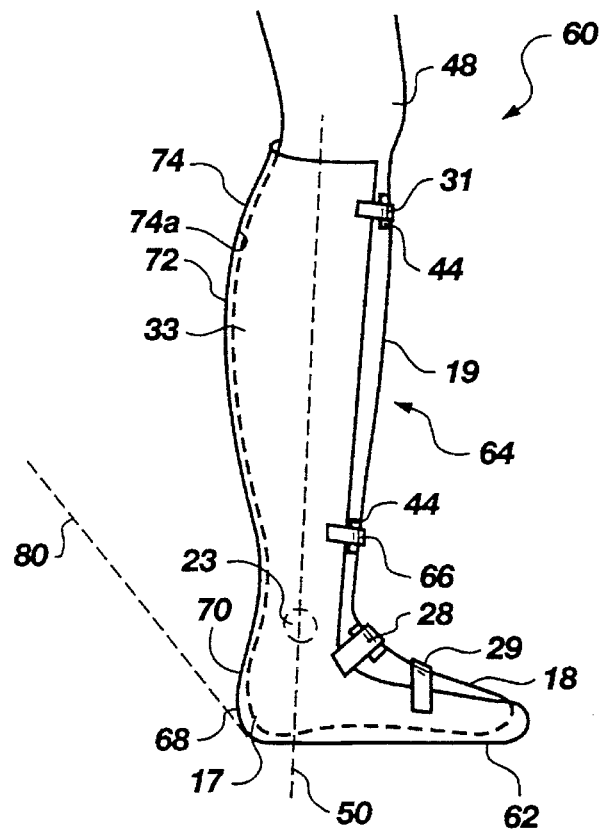
FIG. 6 is a side view of an alternate embodiment of the ankle positioning splint of FIGS. 2–3.

Referring now to FIG. 6, there is shown an alternative embodiment of the foot brace means, as alternative foot brace means 60. This embodiment, although not preferred, is nonetheless in accordance with the principles of the present invention. The alternative foot brace means 60 is load-bearing and includes a bottom plate 62 which is similar in structure and function to the bottom plate 24 of FIGS. 2–3. The alternative foot brace means 60 includes a continuous opening 64 in order to receive the foot 18 and lower leg 19 thereinto. The upper leg strap 31, ankle strap 28, foot strap 29, and shin strap 66, or their equivalent, can be used as foot holding means.

As shown in FIG. 6, the alternative foot brace means 60 includes a rear heel holder 68 defining a heel receiving cavity therein for receiving the heel 17 thereinto when the foot 18 resides in the supported position. The rear heel holder 68 includes an upper portion 70 which forms an acute angle with the bottom plate 62 and resides against and above the heel 17 and closer to the axis 50 of the lower leg 19 than the lower knob 15 of the heel 17, to thereby at least partially encapsulate the heel and block migration of the heel away from the bottom plate 62 when the heel resides in the heel receiving cavity. At least part of the upper portion 70 preferably resides below the ankle 23. It is noted that, in contrast to the acute angle the upper portion 70 makes with the bottom plate 62, the dashed line 80 forms an obtuse angle with the bottom plate 62, not an acute angle.

The alternative foot brace means 60 further includes a rear calf holder 72 defining a calf receiving cavity therein for receiving the larger portion 33 of the calf section of the lower leg 19 thereinto, when the foot 18 resides in the supported position. The rear calf holder 72 includes an upper portion 74 which forms an acute angle with the bottom plate 62 and resides against and above the larger portion 33 of the calf section and closer to the lower leg axis 50 than the larger portion of the calf to thereby at least partially encapsulate said larger portion of the calf and block migration of the lower leg 19, and thus the heel 17, away from the bottom plate 62 when the larger portion of the calf section resides in the calf receiving cavity. The acute angle, as shown in FIG. 6, is formed in that the upper portion 74 includes interior surface means 74a for at least partially facing the bottom plate 62 because of its angled orientation therewith, such that the interior surface means 74a and the bottom plate 62 form the acute angle therebetween, as shown. The alternative foot brace means 60 may be open at the rear portion adjacent the ankle so as not to include the rear heel holder 68 or upper portion 70 thereof, in which case it is the rear calf holder 72 acting alone which accomplishes the objective of the invention. As shown in FIG. 6, the rear calf holder 72 is substantially rigid and is disposed in a substantially fixed orientation with respect to the bottom plate 62.

An alternative embodiment in accordance with the principles of the present invention may include a single, circumscribing calf strap (not shown) in lieu of the calf strap 30 and the upper leg strap 31. The alternative single calf strap would be attached to opposing portions of the foot brace means 25 and could circumscribe the leg but be configured to include a shaped angled rear section which curves upwardly to be supported at the angle α so as to conform to the inherent shape of the upper posterior calf of the extremity 32. A similar single-strap arrangement (not shown) could also be produced in lieu of the heel strap 26 and ankle strap 28. It will thus be appreciated that angled straps can be produced in accordance with the principles of the present invention which do in fact circumscribe the upper calf area or the ankle area so as to provide the specific, non-frictional and downwardly-directed force components which are capable of maintaining the foot 18 in the supported position against the bottom plate 24.

It will be appreciated that many different strap means could be used as the straps 26 and 30. Preferably, the heel strap 26 includes opposing ends which are secured to opposing portions of the foot brace means 25 as shown in FIG. 2. The heel strap 26 seats against the posterior extremity 35 (FIG. 4) such that the opposing ends of the strap 26 extend in a direction substantially perpendicular to the posterior extremity 35. Similarly, the calf strap 30 preferably seats against the posterior leg extremity 32 such that opposing ends of the calf strap 30 extend in a direction substantially perpendicular to the posterior leg extremity 32.

The splint arms 22a–b may include the adjustment structure 40 for adjusting the length of the splint arms to enable the improved splint 20 to be sized with respect to different-sized patients. A further optional embodiment may include that the splint arms 22a–b are selectively pivotally moveable relative to the bottom plate 24, in which case arm locking means 52 is provided for selectively locking the splint arms 22a and 22b at desired pivotally displaced positions relative to the bottom plate 24. This would allow for progressive adjustment of the position of the ankle and foot.

The improved splint 20 may also be partially or even substantially encased in soft energy-absorbing material, shown schematically at 54 in phantom line in FIG. 3. The material 54 is preferably disposed upon exterior portions of the foot brace means 25 to soften any contact the foot brace means might have with other objects.

In accordance with the principles of the present invention as described above, a presently preferred ankle positioning method for maintaining a foot in desired position relative to the corresponding lower leg of the patient to thereby position an ankle of the foot, wherein the foot includes a heel, comprises the steps of:

(a) placing the foot upon a bottom plate of a foot brace means in a supported position, said foot brace means including leg supporting means extending upwardly from the plate and along opposing sides of the lower leg, respectively, said leg support means including lower front and rear openings;

(b) securing ankle strap means to the foot brace means in such a manner that said ankle strap means extends across the lower front opening so as to press against the anterior ankle; and (c) securing heel strap means to opposing portions of the foot brace means in such a manner that said heel strap means extends across the lower rear opening without circumscribing any portion of the foot or leg so as to press against a posterior portion of the foot to thereby aid in preventing substantial migration of the heel away from the bottom plate of the foot brace means.

It will be appreciated that the method defined above may be augmented in many ways which might occur to one possessed of ordinary skill in the relevant art. For example, step (c) may further comprise configuring and arranging the heel strap means to seat firmly against a posterior extremity of the heel which forms a first angle relative to the lower leg, such that a portion of the heel strap means contacting said posterior extremity resides common to said first angle.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An ankle positioning splint for maintaining a patient's foot in a desired position relative to a corresponding lower leg of the patient to thereby position an ankle of the foot, wherein the foot includes a heel, said ankle positioning splint comprising:

load-bearing foot brace means including a bottom plate for supporting the patient's foot in a supported position and leg supporting means extending upwardly from the plate and along opposing sides of the lower leg, respectively, when the foot is supported in the supported position, said leg supporting means further including an upper rear opening;

foot holding means disposed on the foot brace means for pressing against the patient's foot anterior to the ankle; and calf support means secured to opposing portions of the leg supporting means and extending across the upper rear opening thereof for pressing against a posterior portion of the lower leg residing between a knee joint and a larger portion of a calf section of the lower leg, said posterior portion residing forwardly of the larger portion of the calf such that said calf section extends rearwardly to a location beneath and rearward of the portion of the calf support means which is pressing against said posterior portion of the lower leg, to thereby aid in preventing substantial migration of the heel away from the bottom plate of the foot brace means.

2. An ankle positioning splint as defined in claim 1, wherein the foot includes an anterior ankle portion and wherein the heel includes a lower posterior knob extremity, wherein the leg supporting means further includes a lower rear opening, said ankle positioning splint further comprising:

heel support means secured to the foot brace means and extending across the lower rear opening without circumscribing any portion of the foot and without circumscribing any portion of the leg for pressing against a posterior portion of the patient's foot which resides forwardly of the lower posterior knob extremity of the heel such that said lower posterior knob extremity extends rearwardly to a location beneath and rearward of the portion of the heel support means which is pressing against said posterior portion of the foot when said foot is supported in the supported position to thereby aid in preventing substantial migration of the heel away from the bottom plate of the foot brace means.

3. The ankle positioning splint as defined in claim 2, wherein the leg supporting means includes adjustment means for adjusting the length of the leg support means to enable the ankle positioning splint to be sized with respect to different-sized patients.

4. The ankle positioning splint as defined in claim 2, wherein the leg supporting means is selectively pivotally moveable relative to the bottom plate of the foot brace means, the ankle positioning splint further comprising:

locking means for selectively locking the leg supporting means at desired pivotally displaced positions relative to the bottom plate of the foot brace means.

5. The ankle positioning splint as defined in claim 2, wherein the foot brace means includes exterior portions, said ankle positioning splint further comprising:

soft energy-absorbing material disposed upon exterior portions of the foot brace means to soften any contact said foot brace means might have with other objects.

6. The ankle positioning splint as defined in claim 2, wherein the leg support means further includes a lower front opening, and wherein the foot holding means comprises ankle strap means secured to the foot brace means and extending across the lower front opening.

7. The ankle position splint as defined in claim 2, wherein at least a portion of the heel support means resides above the heel and closer to an axis of the lower leg than said heel to thereby block migration of the heel away from the bottom plate of the foot brace means when the foot resides in the supported position.

8. The ankle positioning splint as defined in claim 2, wherein the heel support means is secured to opposing portions of the foot brace means so as to bisect and extend across the rear opening at a location adjacent to the patient's foot when the foot is supported in the supported position such that said heel support means divides said rear opening into upper and lower openings.

9. The ankle positioning splint as defined in claim 2, wherein the foot holding means, the foot brace means, and the portion of the heel support means which presses against the posterior portion of the foot when the foot is supported in the supported position cooperatively define an interior circumferential distance which is less than any circumferential distance of the foot that traverses both a rear-most portion of the lower posterior knob extremity and the anterior ankle portion of the foot.

10. The ankle positioning splint as defined in claim 2 wherein the heel support means includes means for pressing against the heel and exerting a force passing through the heel into a calcaneus of the foot, at least one non-frictional component of said force being conveyed toward the bottom plate of the foot brace means in a substantially parallel alignment with respect to the lower leg.

11. The ankle positioning splint as defined in claim 2, wherein the heel support means is configured and arranged to seat firmly against a posterior extremity of the heel which forms a first angle relative to the lower leg such that a portion of the heel strap means contacting said posterior extremity resides common to said first angle.

12. The foot positioning splint as defined in claim 2, wherein the heel support means comprises a heel strap having opposing ends secured to the opposing portions of the foot brace means, said heel strap being configured and arranged to seat against the posterior extremity such that the ends extend in a direction substantially perpendicular to said posterior extremity.

13. The ankle positioning splint as defined in claim 2, wherein the leg supporting means further includes an upper rear opening, said positioning splint further comprising:

calf support means secured to opposing portions of the leg supporting means and extending across the upper rear opening thereof for pressing against a posterior portion of the lower leg residing between a knee joint and a larger portion of a calf section of the lower leg, to thereby aid in preventing substantial migration of the heel away from the bottom plate of the foot brace means.

14. The ankle positioning splint as defined in claim 13, wherein the calf support means is configured for pressing against said posterior portion of the lower leg without circumscribing the lower leg.

15. The ankle positioning splint as defined in claim 13, wherein the calf support means includes means for exerting a force against said posterior portion of the lower leg, said force including at least one non-frictional component which is conveyed toward the bottom plate of the foot brace means in a substantially parallel alignment with respect to the lower leg.

16. The ankle positioning splint as defined in claim 13, further comprising:

middle support means disposed on the leg supporting means for circumscribing the lower leg, said middle support means residing between the calf support means and the heel support means.

17. The ankle positioning splint as defined in claim 13, wherein the calf support means is configured and arranged to seat firmly against a posterior leg extremity of the lower leg residing between the knee joint of the larger portion of the calf section and which forms a second angle relative to the lower leg, such that a portion of the calf support means contacting said posterior leg extremity resides common to said second angle.

18. The ankle positioning splint as defined in claim 17, wherein the leg supporting means further includes an upper front opening, said positioning splint further comprising:

upper leg support means secured to opposing portions of the leg supporting means and extending across the upper front opening thereof at a location substantially opposite the calf support means.

19. The ankle positioning splint as defined in claim 13, wherein the calf support means comprises a calf strap having opposing ends secured to the opposing portions of the leg supporting means, said calf strap being configured and arranged to seat against a posterior leg extremity of the lower leg residing between the knee joint and the larger portion of the calf section such that the ends extend in a direction substantially perpendicular to said posterior leg extremity.

20. An ankle positioning splint as defined in claim 1, wherein the foot includes a bottom and an anterior ankle portion, said heel including a posterior extremity which forms a first acute angle relative to the bottom of the foot, said ankle positioning splint further comprising:

heel support means attached to the foot brace means and being disposed at an acute angle with respect to the bottom plate of the foot brace means for seating firmly against a posterior portion of the foot when the foot is supported in the supported position such that a portion of the heel support means contacting said posterior portion is maintained to reside substantially common to said first acute angle, to thereby prevent substantial migration of the heel away from the bottom plate of the foot brace means.

21. The ankle positioning splint as defined in claim 20, wherein the heel support means is configured for applying a force directly to the posterior extremity of the patient's heel, said force including at least one non-frictional component which is conveyed toward the bottom plate of the foot brace means in a substantially parallel orientation with respect to the lower leg.

22. The ankle positioning splint as defined in claim 20, wherein the heel support means comprises a heel strap having opposing ends secured to the opposing portions of the foot brace means, said heel strap being configured and arranged to seat against the posterior extremity such that the ends extend in a direction substantially perpendicular to said posterior extremity.

23. The ankle positioning splint as defined in claim 20, further comprising:

calf support means secured to opposing portions of the leg supporting means for pressing against a posterior portion of the lower leg residing between a knee joint and a larger portion of a calf section of the lower leg, to thereby aid in preventing substantial migration of the heel away from the bottom plate of the foot brace means.

24. The ankle positioning splint as defined in claim 20, wherein the foot holding means, the foot brace means, and the portion of the heel support means which presses against the posterior portion of the foot when the foot is supported in the supported position cooperatively define an interior circumferential distance which is less than any circumferential distance of the foot that traverses both a rear-most portion of the lower posterior knob extremity and the anterior ankle portion of the foot.

25. An ankle positioning splint as defined in claim 1, wherein at least a portion of the calf support means resides above the larger portion of the calf section and closer to an axis of the lower leg than said larger portion to thereby block migration of the lower leg, and thus the heel, away from the bottom plate of the foot brace means when the foot resides in the supported position.

26. The ankle positioning splint as defined in claim 1, wherein the calf support means is nonresilient.

27. An ankle positioning splint for maintaining a patient's foot in a desired position relative to a corresponding lower leg of the patient to thereby position an ankle of the foot, said ankle positioning splint comprising:

load-bearing foot brace means including a bottom plate for supporting the patient's foot in a supported position and leg supporting means extending upwardly from the plate and along opposing sides of the lower leg, respectively, when the foot is supported in the supported position; and foot holding means disposed on the foot brace means for pressing against the patient's foot anterior to the ankle;

wherein the foot brace means includes a substantially rigid rear calf holder disposed in a substantially fixed orientation with respect to the bottom plate and defining a calf receiving cavity for receiving a larger portion of a calf section of the lower leg thereinto when the foot resides in the supported position, said rear calf holder including an upper portion having interior surface means for (i) at least partially facing the bottom plate such that said interior surface means and said bottom plate form an acute angle therebetween, and for (ii) residing against and above the larger portion of the calf section to thereby at least partially encapsulate said larger portion of the calf and block migration of the lower leg, and thus the heel, away from the bottom plate of the foot brace means when said larger portion of the calf section resides in the calf receiving cavity.

28. An ankle positioning splint as defined in claim 27, wherein the foot includes a heel having a lower posterior knob extremity, wherein the foot brace means includes a rear heel holder extending upwardly from the bottom plate and cooperatively defining a heel receiving cavity with said bottom plate for receiving the heel thereinto when the foot resides in the supported position, said rear heel holder including an upper portion which forms an acute angle with the bottom plate to thereby at least partially encapsulate the heel and block migration of the heel away from the bottom plate of the foot brace means when the lower posterior knob extremity of the heel resides in the heel receiving cavity.

29. The ankle positioning splint as defined in claim 28, wherein the foot brace means includes a rear calf holder defining a calf receiving cavity for receiving a larger portion of a calf section of the lower leg thereinto when the foot resides in the supported position, said rear calf holder including an upper portion which forms an acute angle with the bottom plate and resides against and above the larger portion of the calf section and closer to an axis of the lower leg than said larger portion of the calf section to thereby at least partially encapsulate said larger portion of the calf and block migration of the lower leg, and thus the heel, away from the bottom plate of the foot brace means when said larger portion of the calf section resides in the calf receiving cavity.

30. The ankle positioning splint as defined in claim 28, wherein the upper portion of the rear heel holder resides against a posterior portion of the patient's foot at a location forwardly of the lower posterior knob extremity such that said lower posterior knob extremity extends rearwardly to a location beneath and rearward of the portion of said upper portion which resides against said posterior portion of the foot when the heel resides in the heel receiving cavity.

31. The ankle positioning splint as defined in claim 28, wherein the foot holding means, the foot brace means, and the upper portion of the rear heel holder cooperatively define an interior circumferential distance which is less than any circumferential distance of the foot that traverses both a rear-most portion of the lower posterior knob extremity and the anterior ankle portion of the foot.

32. The ankle positioning splint as defined in claim 27, wherein the upper portion of the rear calf holder is configured to reside against a posterior portion of the lower leg residing between a knee joint and the larger portion of a calf section of the lower leg, said posterior portion residing forwardly of the larger portion of the calf such that said larger portion of the calf extends rearwardly to a location beneath and rearward of the portion of said upper portion of the rear calf holder which resides against said posterior portion of the lower leg when the patient's foot is supported in the supported position.

* * * * *